(12) United States Patent
Steen

(10) Patent No.: US 6,378,517 B1
(45) Date of Patent: Apr. 30, 2002

(54) COUPLING FOR A BREATHING TUBE SYSTEM

(75) Inventor: Hans-Wilhelm Steen, Zarpen (DE)

(73) Assignee: Dräger Medizintechnik GmbH (DE)

( * ) Notice: Subject to any disclaimer, the term of this patent is extended or adjusted under 35 U.S.C. 154(b) by 0 days.

(21) Appl. No.: 09/573,723

(22) Filed: May 18, 2000

(30) Foreign Application Priority Data

Jun. 2, 1999 (DE) .................................. 299 09 671 U

(51) Int. Cl.$^7$ ............................................. A61M 15/00
(52) U.S. Cl. ............................ 128/200.24; 128/202.27
(58) Field of Search ................... 128/200.24, 200.11, 128/200.14, 202.27, 203.12–203.14, 204.18, 204.22, 204.23, 204.24, 204.25, 207.14, 207.15, 910–912; 604/58; 600/531, 532, 543

(56) References Cited

U.S. PATENT DOCUMENTS

| | | | | |
|---|---|---|---|---|
| 3,661,528 A | * | 5/1972 | Falk ............................. 23/254 |
| 4,456,014 A | * | 6/1984 | Buck et al. .................. 128/719 |
| 4,521,038 A | * | 6/1985 | Cerny ......................... 285/24 |
| 4,558,708 A | * | 12/1985 | Labuda et al. ............... 128/719 |
| 4,997,217 A | * | 3/1991 | Kunze .................... 128/202.27 |
| 5,036,847 A | * | 8/1991 | Boussignac et al. ... 128/207.14 |
| 5,284,160 A | * | 2/1994 | Dryden ................... 128/203.12 |
| 5,404,873 A | * | 4/1995 | Leagre et al. .......... 128/204.18 |
| 5,445,160 A | * | 8/1995 | Culver et al. ........... 128/205.23 |
| 5,465,728 A | * | 11/1995 | Phillips ................. 128/204.17 |
| 5,538,002 A | * | 7/1996 | Boussignac et al. ... 128/207.16 |
| 5,582,161 A | * | 12/1996 | Kee ....................... 128/200.26 |
| 5,720,282 A | * | 2/1998 | Wright ................... 128/207.14 |
| 5,789,660 A | * | 8/1998 | Kodoed et al. .............. 73/23.3 |
| 5,983,896 A | * | 11/1999 | Fukunaga et al. ...... 128/207.14 |
| 6,142,148 A | * | 11/2000 | Weckstrom et al. ... 128/204.22 |
| 6,273,087 B1 | * | 8/2001 | Boussignac et al. ... 128/204.22 |

FOREIGN PATENT DOCUMENTS

EP           0 150 912           1/1985

* cited by examiner

Primary Examiner—John G. Weiss
Assistant Examiner—Teena Mitchell
(74) Attorney, Agent, or Firm—McGlew and Tuttle, P.C

(57) ABSTRACT

A coupling between a breathing tube system is provided with an inner tube and an outer tube. A first connection part is provided with a first connection piece for the outer tube and with a first connection for the inner tube. The first connection is arranged eccentrically in the first connection piece. A second connection part is provided with a second connection piece, which is in flow connection with the first connection piece. The second connection part provides a second connection, which is arranged concentrically in the second connection piece and which is connected to the first connection in terms of flow.

20 Claims, 1 Drawing Sheet

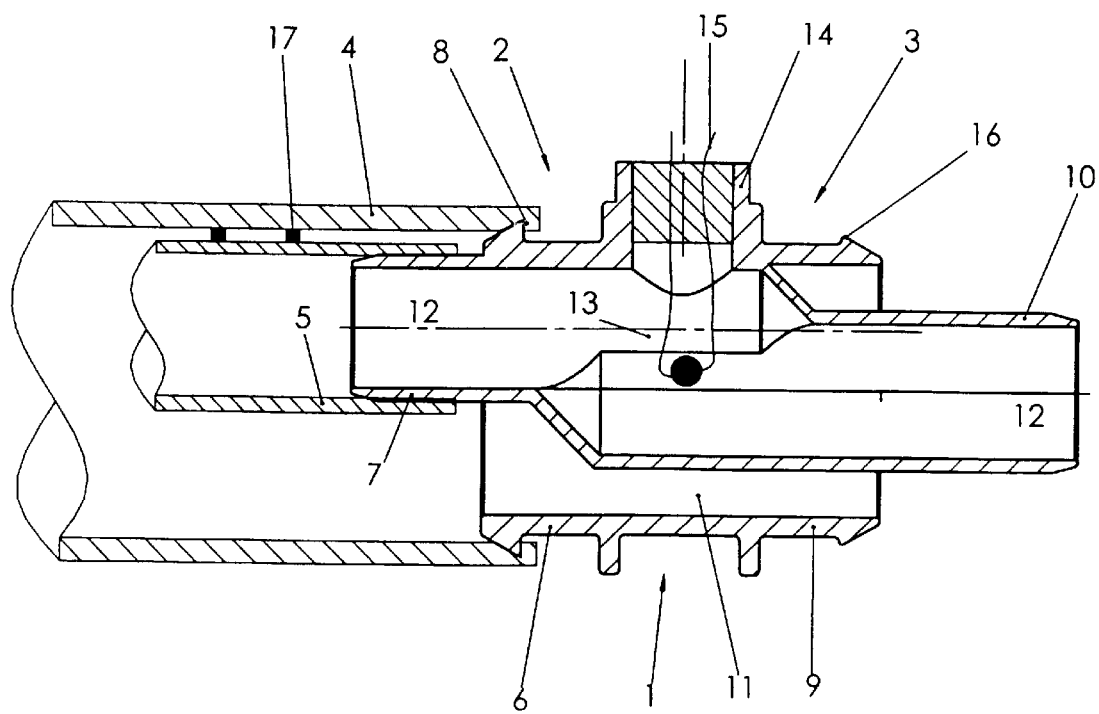

COUPLING FOR A BREATHING TUBE SYSTEM

FIELD OF THE INVENTION

The present invention pertains to a coupling for a breathing tube system with an inner tube and an outer tube.

BACKGROUND OF THE INVENTION

A coupling for a breathing tube system, comprising an outer tube with an inner tube enveloped by the outer tube, has become known from EP 150 912. A first connection part of the coupling has a first connection piece, which is connected to the outer tube, and a connection for the inner tube, which is arranged eccentrically on the first connection piece, is located within the first connection piece. The second connection piece of the coupling is provided with an inner cone and is used for connection to a patient tube or a gas mask. The patient receives the fresh breathing gas from the inner tube and breathes the exhaled gas back into the outer tube. The breathing gases are mixed in the area of the second connection part, because there is no separation between the different types of gas. In addition, the fresh breathing gas flowing in via the inner tube flows off unused into the outer tube during the phase of exhalation.

SUMMARY AND OBJECTS OF THE INVENTION

The primary object of the present invention is to improve a coupling of this type such that the breathing gas being delivered by the breathing tube system can be fed to the user over paths that are separated from one another in terms of flow.

According to the invention, a coupling between a breathing tube system is provided with an inner tube and an outer tube. A first connection part is provided with a first connection piece for the outer tube and with a first connection for the inner tube. The first connection is arranged eccentrically in the first connection piece. A second connection part is provided with a second connection piece, which is in flow connection with the first connection piece. The second connection part provides a second connection, which is arranged concentrically in the second connection piece and which is connected to the first connection in terms of flow.

A measuring connection, which opens into a flow channel surrounded by the connections, may be present in the connection area between the first connection and the second connection.

The length of the first connection may be selected to be such that it projects beyond the first connection piece. The length of the second connection may be selected to be such that it projects beyond the second connection piece. The first connection piece may be provided with a first undercut for fixing the outer tube. The second connection piece may have a second undercut.

It is especially advantageous to provide a measuring connection, which opens from the outside into the flow channel surrounded by the connection, between the inner connections of the coupling. For example, a temperature-measuring sensor, with which the temperature of the gas flow flowing through the connections can be measured, may be inserted into the measuring connection. As an alternative to the temperature measurement, the measuring connection may also be used for breathing gas analysis with an exhausting gas analyzer.

For the case of temperature measurement on the coupling, it is advantageous to design the flow channel as a measuring chamber with an enlarged cross-sectional area compared with the internal diameter of the connections in the area of the measuring connection. Smoothing of the flow in the area of the measuring connection is thus achieved. The enlargement of the cross section is obtained by the measuring chamber being arranged in the overlapping area of the eccentrically fastened first connection with the concentric second connection. The cross-sectional areas add up in the overlapping area due to the radial offset of the connections.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the drawing:

The only FIGURE is a schematic longitudinal sectional view showing a coupling with a first connection part and a second connection part.

DESCRIPTION OF THE PREFERRED EMBODIMENT

Referring to the drawings in particular, the FIGURE schematically shows the longitudinal section of a coupling 1 with a first connection part 2 and a second connection part 3 for connecting an outer tube 4 and an inner tube 5 surrounded by the outer tube to a user, not shown in the FIGURE. For fastening the tubes 4, 5, the first connection part 2 is provided with a first connection piece 6 for the outer tube 4 and with a first connection 7 for the inner tube 5. The connection is fastened eccentrically within the first connection piece 6. The length of the first connection 7 is selected to be such that it projects beyond the first connection piece 6, so that the inner tube can first be pushed over the connection 7 before the outer tube 4 snaps into an undercut 8 located on the first connection piece 6. The user-side, second connection part 2 of the coupling 1 comprises a second connection piece 9 and a second connection 10 arranged concentrically therein. The length of the second connection 10 is likewise selected to be such that it projects beyond the second connection piece 9. The second connection part 3 can thus be connected to the user, not shown in the FIGURE, via the second connection 10 before the gas connection with the outer tube 4 is established via the second connection piece 9. The coupling 1 is mechanically fixed on the user via a second undercut 16 on the second connection piece 9. The connection pieces 6, 9 and the connections 7, 10 make possible the separation of the gas flows in the tubes 4, 5 according to their type, and an axial rotation of the coupling 1 in relation to the connection on the user is possible due to the concentric arrangement of the second connection 10 within the second connection piece 9. The connection between the connection pieces 6, 9 in terms of flow is established via a gas channel 11. The connections 7, 10 surround a flow channel 12, which is expanded into a measuring chamber 13 in the overlapping area of the connections 7, 10. The measuring chamber 13 is provided with a measuring connection 14 for a temperature sensor 15. Smoothing of the gas flow in the area of the temperature sensor 15 is achieved due to the enlarged cross-sectional area of the flow channel 12 within the measuring chamber 13.

To improve the stability against kinking, the inner tube 5 is arranged eccentrically in the outer tube 4 and is connected to the inner wall of the outer tube 4 via bonds 17. A defined position of the inner tube 5 in the outer tube 4 is obtained due to the bonds 17.

While a specific embodiment of the invention has been shown and described in detail to illustrate the application of the principles of the invention, it will be understood that the invention may be embodied otherwise without departing from such principles.

What is claimed is:

1. A breathing tube system coupling, comprising;
   an inner tube;
   an outer tube;
   a first connection part with a first connection for said outer tube and with a first connection for said inner tube, said first connection for said inner tube being arranged eccentrically in said first connection for said outer tube;
   a second connection pan with a second outer connection in flow connection with said first connection for said outer tube, and with a second inner connection arranged concentrically in said second connection part and which is in flow connection with said first connection for said inner tube.

2. A coupling in accordance with claim 1, further comprising a measuring connection, which opens into a flow channel surrounded by said first connection for said inner tube and said second inner connection, said measuring connection being provided in a connection area between said first connection for said inner tube and said second inner connection.

3. A coupling in accordance with claim 2, wherein said flow channel has an internal diameter, said connection area includes a measuring chamber with a cross-sectional area larger than a said internal diameter of said flow channel.

4. A coupling in accordance with claim 3, wherein a length of said first connection for said inner tube is selected to be such that it projects beyond said first connection for said outer tube.

5. A coupling in accordance with claim 1, wherein a length of said second inner connection is selected to be such that it projects beyond said second outer connection.

6. A coupling in accordance with claim 1, wherein said first connection for said outer tube is provided with a first undercut for fixing said outer tube.

7. A coupling in accordance with claim 1, wherein said second outer connection has a second undercut.

8. A breathing tube system coupling, comprising:
   an inner tube;
   an outer tube;
   a first connection part with a first outer connection piece for said outer tube and with a first inner connection piece for said inner tube, said first inner connection piece for said inner tube being arranged eccentrically in said first outer connection piece;
   a second connection part with a second outer connection piece in flow connection with said first outer connection piece, and with a second inner connection piece arranged concentrically with respect to said second outer connection piece and which is in flow connection with said first inner connection piece.

9. A coupling in accordance with claim 8, wherein said first connection part and said second connection part are formed as a single homogenous element.

10. A coupling in accordance with claim 8, further comprising a measuring connection, which opens into a flow channel surrounded by said first inner connection piece and said second inner connection piece, said measuring connection being provided in a connection area between said first inner connection piece and said second inner connection piece.

11. A coupling in accordance with claim 10, wherein said flow channel has an internal diameter, said connection area includes a measuring chamber with a cross-sectional area larger than said internal diameter of said flow channel.

12. A coupling in accordance with claim 8, wherein a length of said first inner connection is selected to be such that it projects beyond said first outer connection.

13. A coupling in accordance with claim 8, wherein a length of said second inner connection is selected to be such that it projects beyond said second outer connection.

14. A coupling in accordance with claim 8, wherein said first outer connection is provided with a first undercut for fixing said outer tube.

15. A coupling in accordance with claim 8, wherein said second outer connection has a second outer connection undercut.

16. A coupling in accordance with claim 8, wherein:
   said first inner connection piece defines a first inner coupling passage in communication with said inner tube and said second inner connection piece.

17. A coupling in accordance with claim 16, wherein:
   said first outer connection piece has a circular shape,
   said second outer connection piece has a circular shape;
   said first outer connection piece defines a first outer coupling passage;
   said first inner coupling passage is arranged eccentrically in said fit outer coupling passage;
   said second outer connection piece defines a second outer coupling passage;
   said second inner connection piece defines a second inner coupling passage, said second inner coupling passage is arranged concentrically in said second outer coupling passage;
   said first outer coupling passage is in communication with said second outer coupling passage;
   said first inner coupling passage is in communication with said second inner coupling passage.

18. A coupling in accordance with claim 8, wherein:
   said first inner connection piece has a circular shape, said circular shape of said first inner connection piece is arranged eccentrically in said first outer connection piece.

19. A coupling in accordance with claim 8, wherein:
   said second inner connection piece has a circular shape, said circular shape of said second inner connection piece is arranged concentrically in said second outer connection piece.

20. A coupling in accordance with claim 8, wherein:
   said second inner connection piece defines a second inner coupling passage in communication with said first inner connection piece.

* * * * *